United States Patent [19]
Miller et al.

[11] Patent Number: 5,668,082
[45] Date of Patent: Sep. 16, 1997

[54] POLYOLEFINIC ADJUVANTS

[75] Inventors: Deborah L. Miller; John C. Miller, both of Hawthorn Woods, Ill.

[73] Assignee: Deerpoint Industries, Inc., Hawthorn Woods, Ill.

[21] Appl. No.: 696,732

[22] Filed: Aug. 14, 1996

Related U.S. Application Data

[63] Continuation-in-part of Ser. No. 416,617, Apr. 5, 1995.
[51] Int. Cl.$^6$ .................... A01N 25/24; A01N 25/30
[52] U.S. Cl. .................... 504/113; 504/116; 514/937; 424/407
[58] Field of Search ................. 504/116, 113; 514/937; 424/407

[56] References Cited

U.S. PATENT DOCUMENTS

| 4,156,321 | 5/1979 | Capizzi et al. | 43/114 |
| 4,397,681 | 8/1983 | Boehme | 71/106 |
| 5,256,419 | 10/1993 | Roe et al. | 424/407 |
| 5,300,255 | 4/1994 | Campbell et al. | 252/351 |

*Primary Examiner*—S. Mark Clardy
*Attorney, Agent, or Firm*—John G. Premo

[57] ABSTRACT

A biocide composition including an active material selected from the group consisting of insecticides, herbicides, fungicides and rodenticides, and an aqueous polyolefinic emulsion. Alternatively, the composition can include an active material such as a nutrient or plant growth regulator and the polyolefin can be present in other suitable media to provide, in any embodiment, improved retention/sticker properties.

12 Claims, 7 Drawing Sheets

POLYOLEFINIC ADJUVANTS

RELATED APPLICATIONS

This application is a continuation-in-part of our pending application Ser. No. 08/416,617 filed Apr. 5, 1995 by Deborah L. Miller and John C. Miller under the title, Polyolefinic Adjuvants.

FIELD OF THE INVENTION

The invention relates to adjuvants for a variety of biocidial materials and the method for using these materials.

BACKGROUND OF THE INVENTION

This invention relates generally to polyolefinic adjuvants and, more particularly, to polyolefinic compositions, solutions and emulsions for enhancing the efficacy of agricultural, horticultural biocides and nutrients.

The effectiveness of any topical agricultural or horticultural treatment depends primarily upon two factors: (1) The retention of the treatment on the plant surface for a time sufficient to achieve the desired result; and (2) coverage of the treatment to provide uniform benefit over the entire plant surface. In the parlance of the industry, a "sticker" is a material that increases the retention of sprays or dust deposits on plants by resisting various weather factors. A sticker is further defined as a substance which increases the firmness of attachment of finely-divided solids or other water-soluble or -insoluble materials to a solid surface, and which may be measured in terms of resistance to time, wind, water, mechanical or chemical action. Typically, stickers are substances such as latex or other adhesives that improve attachment of an active ingredient to sprayed surfaces. In the pesticidal context, stickers protect the active pesticide ingredient from wash-off due to rainfall, heavy dew or irrigation, and help prevent pesticide loss from wind or leaf abrasion.

Likewise, the industry defines a "spreader" as a substance which increases the area that a given volume of liquid will cover. Spreaders are also known as film extenders, wetting agents or surfactants. Notwithstanding the difference in terminology, all such substances reduce the surface tension of spray droplets, increase surface wetting and enhance coverage. Using terminology most often associated with surfactants, use of anionic spreader on a plant increases the resistance of an active material to removal by rain, dew or irrigation. Anionics also prevent the active ingredient from being readily absorbed through plant cuticles, and such materials are, therefore, used when the effectiveness of the active material depends upon it remaining on the outer surface of the plant. Alternatively, non-ionic spreaders can be used to increase the transport of an active material through plant cuticles and are, therefore, recommended for use with systemic herbicides, nutrients and the like.

As mentioned above, a sticker/spreader combination is used frequently in conjunction with or as an adjuvant with various active materials, which term as used herein and in the claims includes biocides, herbicides, fungicides, insecticides, rodenticides, nutrients, plant growth regulators, repellents and the like. The adjuvant spreads the active material more evenly over a plant surface and, if not to promote absorption, to keep it there for a longer period of time. The search for an efficient, effective sticker/spreader meeting these basic requirements has been an on-going concern in the art. Various approaches and chemical systems have been used with certain success, but each has limited utility due to specific, well-defined problems, most of which are related to retention deficiencies and/or incompatibility with the active material or solutions thereof.

Polyvinylpyrrolidones have been used extensively, but are observed to behave more as an encapsulation agent than a sticker. These materials tend to dissolve only very slowly in water and the cost is prohibitive. The various polymenthenes and/or pinenes provide reasonable sticking properties, but are difficult to emulsify. Such materials are relatively expensive and tend to be unstable over time, providing an inadequate shelf life under most storage conditions.

Polyethylenes are, perhaps, the most widely used sticker materials, but are—as with the polymenthenes—costly and difficult to emulsify. Performance is also problematic in that the films formed tend to wash off. Polymethylacrylates have also been used, but with limited success. These resins are highly insoluble and form a coating incompatible with many tank mixes. Various surfactants are also used, alone, and promoted as sticker/spreaders. However, as discussed above, without a sticker component, they do not afford retention of the treatment or active material on the plant surface for a sufficient time.

In summary, a considerable number of drawbacks and problems exist in the art relating to stickers and sticker/spreaders. There is a need for an improved sticker and/or sticker/spreader composition to more fully take advantage of the benefits available through use of various biocides, herbicides, fungicides, insecticides, nutrients, repellents and the like.

OBJECTS OF THE INVENTION

It is an object of this invention to provide a polymeric system for use as a retention agent or a retention/surface active composition, in conjunction with an active material/ingredient, overcoming the problems and deficiencies of the prior art.

It is also an object of this invention to provide a polyolefin for use, included but not limited to, as a sticker composition or in a sticker/spreader combination—with an active material/ingredient.

Another object of the present invention is to provide for an olefinic homo- or co-polymer, for use as contemplated herein, which can be used with comparable results either neat, dissolved in a suitable organic solvent, or as an aqueous oil-in-water emulsion, whereby when applied to a subject surface shows improved resistance to environmental factors.

Another object of the present invention is to provide a polyolefinic system which is readily emulsified in water, with a variety of suitable surfactants, but does not re-emulsify after application.

Another object of the present invention is to provide a polymeric system, achieving these and other objects discernible to those skilled in the art, which has, essentially, the chemical structure, function, and morphology of a polyolefin, and meets a definition of a polyolefin, notwithstanding the method or process by which it is prepared.

Another object of the present invention is to present a polyolefinic system as a sticker composition or in a sticker/spreader combination—with active materials which can be designed at the molecular level to provide, through known manufacturing and process techniques and/or reactions, specific structural and performance features.

Another object of the present invention is to provide biocidic, plant growth, nutrient, and defoliant compositions, among others, containing the polyolefinic systems of the invention which are distributable more evenly over a subject surface and retained thereon for a longer period of time.

Another object of the present invention is to provide a polymeric system for use as a retention agent or a retention/surface active composition which permits improved, more efficient and economical methods of application.

Other objects, features and advantages of the present invention can be derived from the following description of the invention, including the preferred embodiments thereof, taken in conjunction with the accompanying examples and figures.

SUMMARY OF THE INVENTION

This invention is an effective, efficient sticker composition and/or sticker/spreader adjuvant combined with active materials used in the agricultural and horticultural industry.

An important aspect of this invention is the improved sticking function available to the biocide or like composition through incorporation of a low molecular weight polyolefin hydrocarbon resin. Such resins, whether used alone or in conjunction with a spreader component, can be used in quantities approximating half that required with polymeric stickers/spreaders of the prior art to achieve comparable or improved results. The amount should be at least a film forming amount e.g. sufficient to coat the surface to which it is applied with a thin tacky film. When used with spreader component, the polyolefin resin forms a stable aqueous emulsion infinitely dilutable in water, rendering it suitable for spray delivery. Alternatively, the polyolefins dissolve readily in various organic solvents, for use directly or as aqueous emulsions. Low molecular weight embodiments can be used neat.

The Invention

The present invention is a composition, including (1) an active material, preferably, selected from the group consisting of insecticides, herbicides, fungicides and rodenticides; and (2) a low molecular weight polyolefin resin having a molecular weight not greater than about 30,000. These resins are preferably combined with an emulsifier sticker preferably in the form of a oil-in-water emulsion. The polyolefin resins consist essentially of lower alkyl substituted and preferably methyl-substituted polyolefins. In more preferred embodiments, the polyolefin is selected from the group consisting of isobutylene homo- and co-polymers having a molecular weight of about 300–30,000. When present as an isobutylene co-polymer, the polyolefin may include co-monomers selected from the group consisting of butylene, styrene, butadiene, isoprene and combinations thereof. In highly preferred embodiments, the polyolefin is a co-polymer of isobutylene and butylene. Whereas the co-polymer can have a molecular weight of about 300–30,000, more desirable polymers have a molecular weight of about 900–3,000.

The present invention also includes solid surfaces such as vegetative material having applied thereto at least a thin film of the composition containing the adjuvant as described above. The polyolefin per se or in a liquid medium forms a water-insoluble deposit on the vegetative surface upon drying.

Lastly, the invention comprises the method of coating solid surfaces with the compositions of the invention to provide superior protection to such surfaces against the ravages of pests of the types controlled by application of the active materials.

The Polyolefins

The preferred low molecular weight polyolefins, which are isobutylene polymers, while capable of being prepared from relatively pure monomer sources are desirably those resins prepared from refinery hydrocarbon streams that are rich in isobutylene and with the remainder thereof comprising mixtures of butenes. One such source of these polymers are those polymers made available from AMOCO and are described in their trade literature as being a polybutene which contains isolated double bond which makes it highly stable. These resins are said to be made from an isobutylene rich stream over a catalyst. These polymers are similiar to pure polyisobutylene even though they contain some 1 and 2-butenes. Polymers of this type may be further characterized by the fact that the isobutylene content thereof is greater than 50 mole percent.

The molecular weight of the polyolefins can be determined by methods well-known to those skilled in the art, in particular by the AM-S 320.06 test method. The molecular weight of any given polyolefin is theoretically unlimited and the higher molecular weight embodiments can be accessed through straight-forward modifications of synthetic procedures also well-known to those skilled in the art and made aware of this invention. At molecular weights higher than 30,000, solubility of the olefinic sticker is problematic and, in the emulsion context, the amount of surfactant required is cost-prohibitive.

In highly preferred embodiments, the polyolefinic sticker component is a polyisobutylene/butene co-polymer, with a molecular weight of about 1,300 or, alternatively, a polyisobutylene-butene co-polymer, having a molecular weight of about 2,500. Both embodiments, among others, are commercially available from Deerpoint Industries, Inc. of Hawthron Woods, Ill. under the DPI S100 and DPI 200 trademarks, respectively.

Oil-in-Water Emulsions

Although the sticker component of the present invention can be used neat, or in conjunction with an active material, numerous applications require dissolution in a suitable organic solvent or emulsification into water. With respect to the latter and given the insoluble nature of these materials, emulsification is accomplished through use of a suitable emulsifier-surfactant, which further acts as a spreader or film extender for uniform application on the subject surface. Depending upon the desired use and effect of the active material, the surfactant may be either ionic or non-ionic. In preferred embodiments, such as with the DPI S100 and DPI S200 commerical products, as described above, one of many available sulfonate surfactants is employed, the choice of which depends, in part, upon cost and compatibility with the active material or the liquid medium within which it is present. The DPI S100 contains about 45–55% by weight of the polyisobutylene-butene polymer, about 0.1% of sodium lauryl sulfate or nonylphenol Rx 7–9 moles of ethylene oxide and with the balance being water.

The Spreading Agents Oil-in-Water Emulsifiers

The emulsifiers which act as spreading agents and to form and stabilize the oil-in-water emulsions of the invention should have an HLB number of at least 8. The HLB number as it relates to emulsions is described in the text, Emulsions and Solubilization K. Shinoda and S. Friberg, John Wiley & Sons, 1986 Chapter 2. They should be prepared so that the particle size of the emulsion is about 1 micron or less. Anionic and non-ionic types are the most preferred types.

Illustrative of typical surfactants that can be used in preparing the oil-in-water emulsions used in the practice of the invention are: Petroleum or paraffinic sulfonates (i.e. alkyl or aromatic) such as dodecylbenzene sulfonate, lauryl sulfonate, etc. Ethoxylated alcohols, such as ethoxylated nonyl phenols or ethoxylated decyl alcohol.

Specific examples of surfactants, as approved in the Federal Register under 40CFR180.1001: Alkyl (C6–C24) benzene sulfonic acid and its ammonium, calcium, magnesium, potassium, sodium, and zinc salts. Alpha-alkyl (C12–C15)-omega-hydroxypoly (oxyethylene) sulfate, ammonium, calcium, magnesium, potassium, sodium, and zinc salts; the poly (oxyethylene) content averages 3 moles). Alpha-alkyl (C6–C14)-omega-hydroxypoly(oxypropylene) block copolymer with polyoxyethylene; polyoxypropylene content is 1–3 moles; polyoxyethylene content is 4–12 moles; average molecular weight is about 635. Alpha-(p-Alkylphenyl)-omega-hydroxypoly(oxyethylene) produced by the condensation of 1 mole of alkyl-phenol (alkyl is a mixture of propylene tetramer and pentamer isomers and averages C13) with 6 moles of ethylene oxide. Alkyl (C8–C13) sulfate and its ammonium, calcium, isopropylamine, magnesium, potassium, sodium, and zinc salts. Many others.

The emulsifier-stickers when used to prepare concentrated emulsions, e.g. those having polyolefin polymer concentrations greater than about 10% by weight are usually used in amounts ranging from as little as 0.005% to about 10% based on the weight of the emulsion. Typically, for emulsions containing 20% or more by weight of the polyolefin polymer the range normally will be between 0.05–5%. For dilute emulsions the amount of the emulsifier is adjusted to be effective with the type and amount of polyolefin polymer. Concentrated emulsions may contain as much as 60% or more of the polyolefins.

The emulsions most useful in the practice of the invention are concentrated emulsions which allows for greater economy in their shipping and handling. These emulsions are readily diluted by combining them with additional water.

The concentrated forms may be used when added to polyolefin polymers or concentrates thereof. In many instances the end user will dilute the concentrated emulsions for addition to field strength active materials such as insecticides and herbicides.

In some instances the active materials are furnished dissolved or suspended in a non-ionic surfactant which is a spreading agent or oil-in-water emulsifier. In such cases, for the purposes of this disclosure, such system utilize the non-ionic surfactant as both a solvent and as an emulsifier. With such products it may be considered and assumed that a portion of the surfactant acts as an oil-in-water emulsifier and the balance functions as a solvent or suspending media.

The Solvents

The solvents used to dissolve or suspend the Active materials may be selected from a large number of organic liquids. One preferred class are the vegetable oils particularly the so called seed oils, e.g. rape seed, cotton seed, sunflower seed oil and the like. Other vegetable oils are also used such as corn and soybean oils. In addition to the vegetable oils other oils such as those derived from the refining of petroleum are also used. When the polyolefins are prepared as solutions or suspensions in oils the oils should be used if possible so that compatibility with the active material is maximized.

Dosage of the Adjuvants

A specific use and/or application of the sticker/adjuvant compositions of this invention will, in part, determine the particular embodiment or formulation employed. For example, ground application can entail use of various diluted full-volume or concentrated sprays. With respect to the former, using DPI S100 as a standard, the dosage would be 8–16 fluid ounces of the composition, solution, or emulsion, more or less depending upon the coverage and effect desired, per 100 gallons of water or active material/agent is effective. For concentrated sprays, the same volumes can be used, without dilution, as required to wet foliage. Aerial applications typically require lower volumes-normal use rates are about 4–8 fluid ounces per acre, but may meet or exceed 16 fluid ounces per acre. If applied with a spray, it is advantageous to add the inventive composition, solution, or emulsion as the spray tank is filled—with agitation, if possible. Pre-mixing is not required before addition to the spray tank because the polyolefins of this invention are stable during storage, whether neat, in solution or as part of an aqueous emulsion. The quantity and/or concentration will also vary with water hardness, equipment characteristics, temperature, and type (surface characteristics) of foliage to be treated. The amount always should be such to provide a thin film of the adjuvant on the surface to which it is applied.

EXAMPLE 1

Two polyolefin compositions of this invention were compared with a widely-used standard of prior art, a mixture of alkylphenoxy polyethoxy ethanols in cottonseed oil available under the CMR trade designation, to determine the retention/longevity of NORDOX, the trade name of a common, commercial copper oxide fungicide. The labeled, advised rate of NORDOX with or without the respective adjuvant, as shown below, was applied to four separate ornamental trees, using a hand-held carbon dioxide, backpack-type sprayer with two-foot booms and dual nozzles. NORDOX was used, alone, as a control. The DPI S100 (FIG. 1A) and DPI S200 (FIG. 1B) sticker/spreaders of this invention were used at a concentration of 8 fluid ounces per 100 gallons of NORDOX. The CMR product was used at a concentration of 32 fluid ounces per 100 gallons of NORDOX.

Figure 1A:
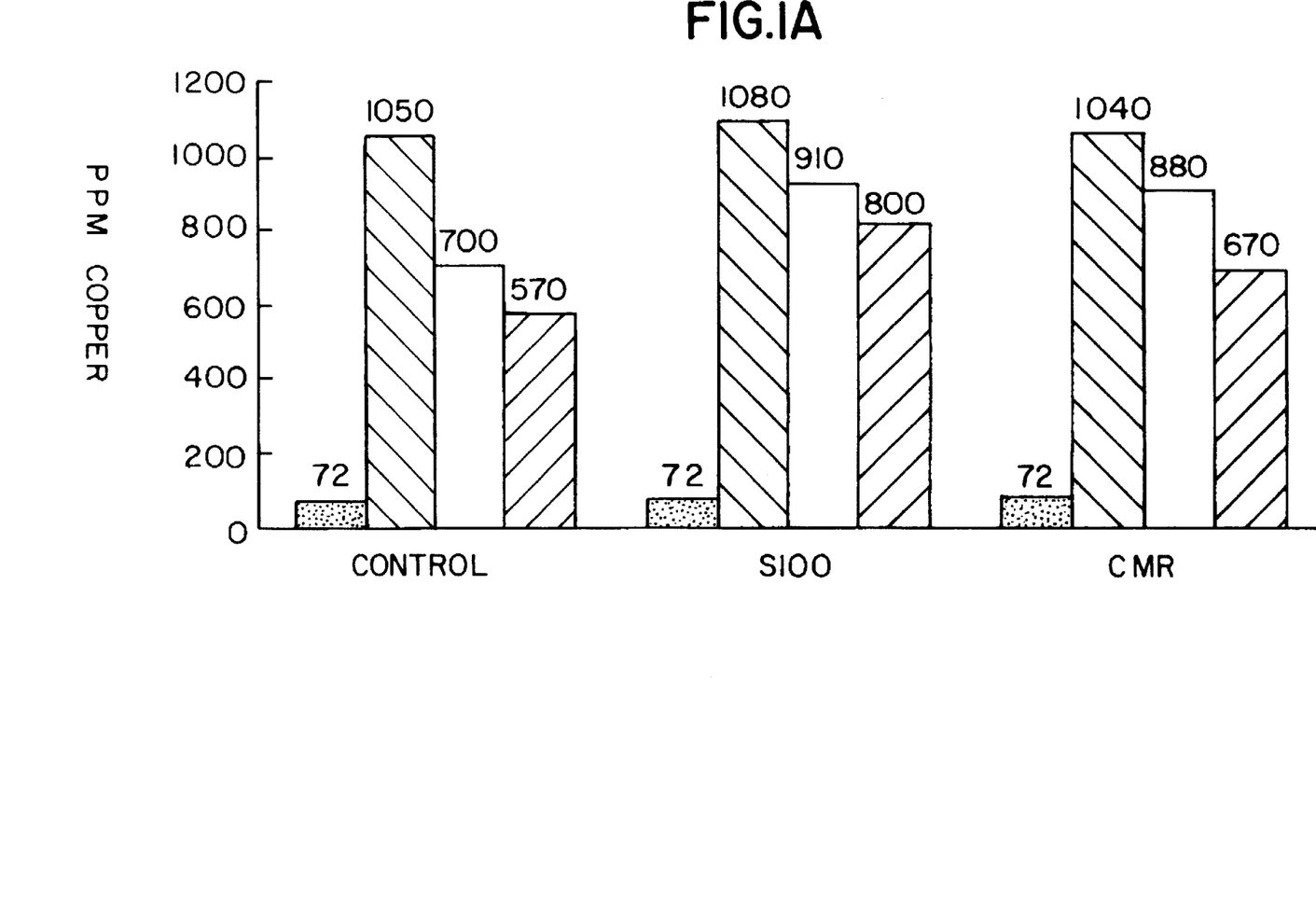
FIG. 1A graphically illustrates, by comparison, the levels and/or retention of Cu on ornamental tree leaves sprayed with the fungicide NORDOX, alone, with a prior art product, and with an olefinic copolymer (DPI S100) in accordance with this invention—before spraying (solid), post-spray (///), at two weeks (open), and at four weeks (\\\)
Figure 1B:
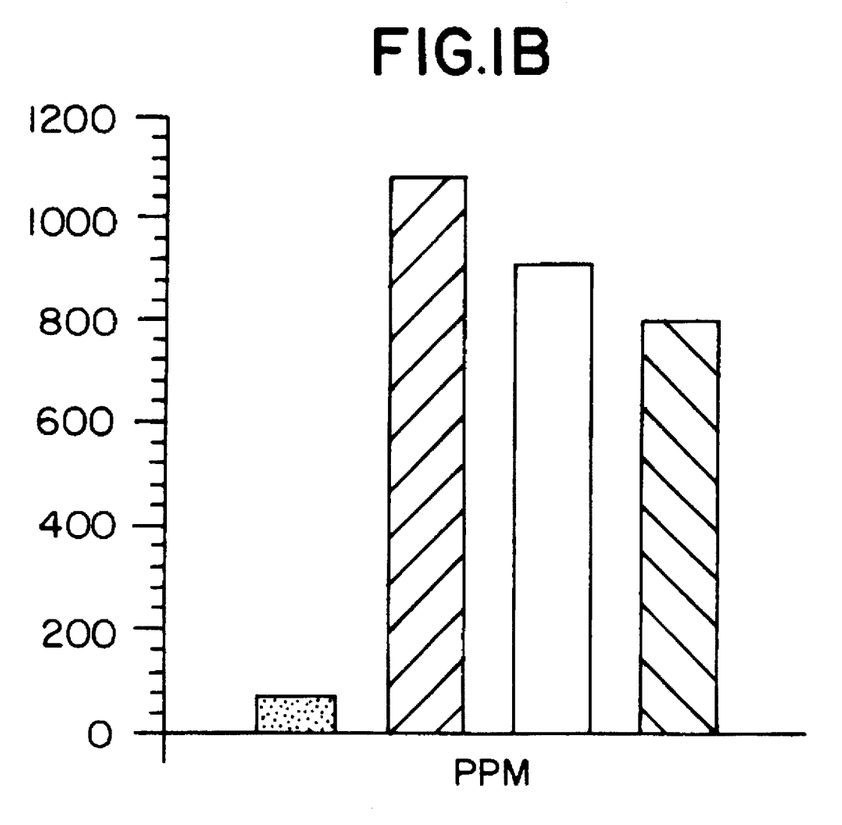
FIG. 1B graphically extends the comparison of FIG. 1A to include another olefinic copolymer (DPI S200) of the present invention before spraying (solid), post-spray (white dots), at two weeks (black dots), and at four weeks (xxx)

A random sampling of leaves were prepped according to standard procedures and analyzed by atomic absorption spectroscopy to determine a base Cu level (72 ppm). Immediately after application, leaves were randomly pulled, prepped and analyzed to determine the increase in Cu levels. The sampling and analysis was repeated at two weeks, then at four weeks to compare NORDOX retention. The results, summarized in FIGS. 1A and 1B, show conclusively that the polyolefins of this invention at concentrations four times lower than the prior art—retain more active material/ingredient for longer periods of time. In particular, using the DPI S100 sticker/spreader, Cu retention was observed after four weeks to be 20% greater than the retention available through use of the prior art compositions.

EXAMPLE 2

The results of Example 1 were extended to nutrient retention, with similiar effect. The DPI S100 polyolefin sticker/spreader, in accordance with this invention, was compared with the CMR standard of the prior art. The compositions were tested in conjunction with a cherry orchard treatment comprising the zinc salt of ethylenediaminetetraacetic acid (nutrient), DIAZINON (insecticide) and CENIPHOS (phosphoric acid, to adjust pH and as a nutrient source). In all treatments tested, both the intial zinc nutrient and DIAZINON concentrations were 1 pound per 100 gallons (2.5 pounds per acre over the 10-acre cherry orchard test plot), and the intial CENIPHOS concentration was 1 gallon per 100 gallons.

The ten-acre plot was divided into five two-acre sub-plots, with control sub-plots separating each of three test sub-plots. The cherry trees in each control sub-plot were sprayed with the nutrient and insecticide treatment at the concentrations described above. Trees of the first test plot were sprayed with a CMR-modified (8 fluid ounces per 100 gallons) nutrient/insecticide treatment. The second test plot was sprayed with DPI S100-modified (8 fluid ounces per 100 gallons) nutrient/insecticide treatment. Trees of the third test plot were sprayed with a DPI S100-modified (4 fluid ounces per 100 gallons) nutrient/insecticide treatment.

A random sampling of leaves were prepped according to standard procedures and analyzed by atomic absorption spectroscopy to determine a base Zn level (13–16 ppm). Approximately one month after application, 100 cherry leaves were selected from each test plot, the sampling technique involving leaves from every other tree in the plot and from alternate sides of each row. In a similiar fashion, 100 cherry leaves were sampled at approximately 3 months. After each sampling, the leaves were prepped and analyzed to determine Zn levels and compare nutrient retention.

Figure 2A:
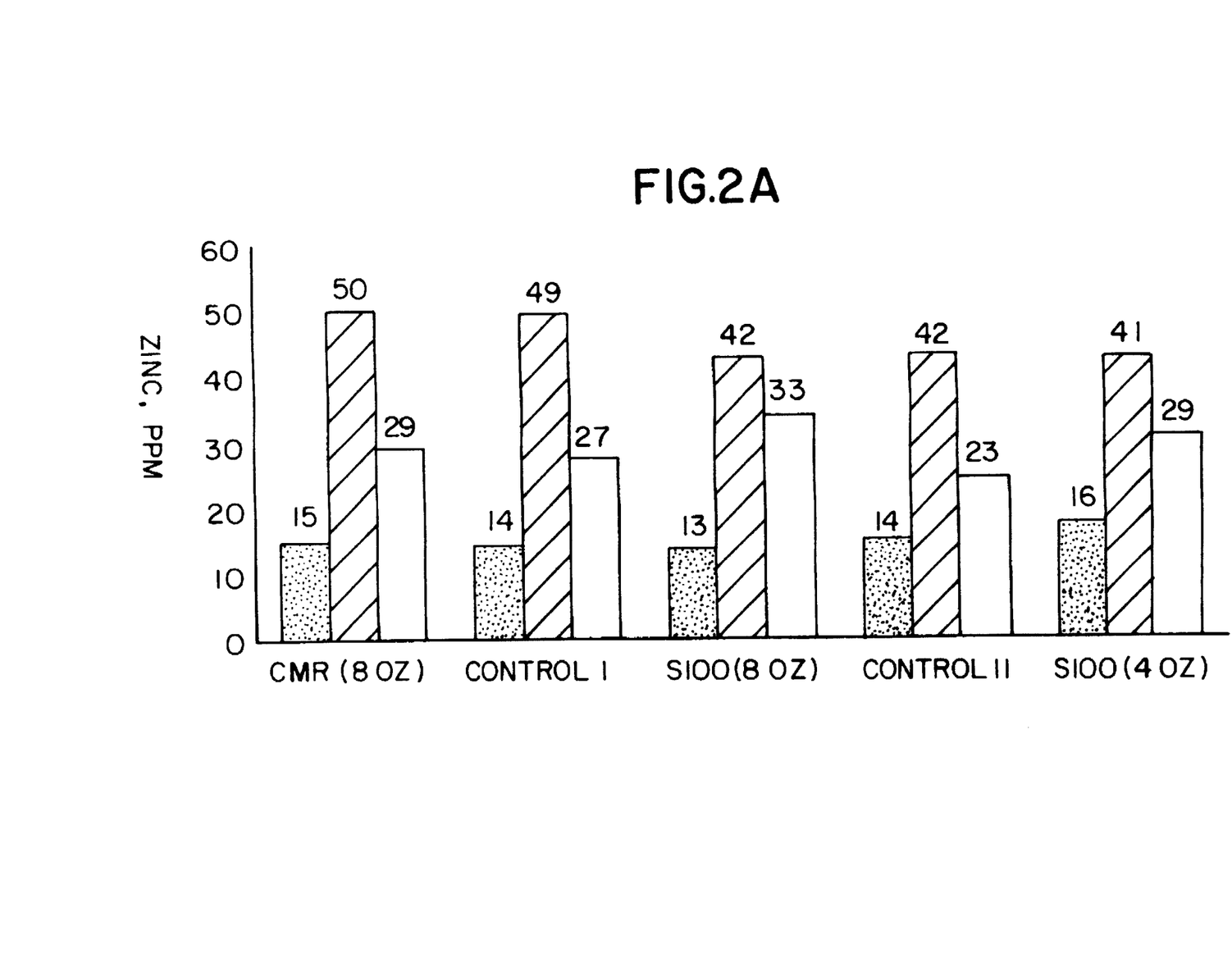
FIG. 2A graphically illustrates, by comparison, the levels and/or retention of Zn on cherry tree leaves sprayed with a standard nutrient/pesticide treatment, alone, with a prior art product, and with different concentrations of an olefinic copolymer (DPI S100) in accordance with this invention—before spraying (solid), at one month (///), and at three months (xxx)
Figure 2B:
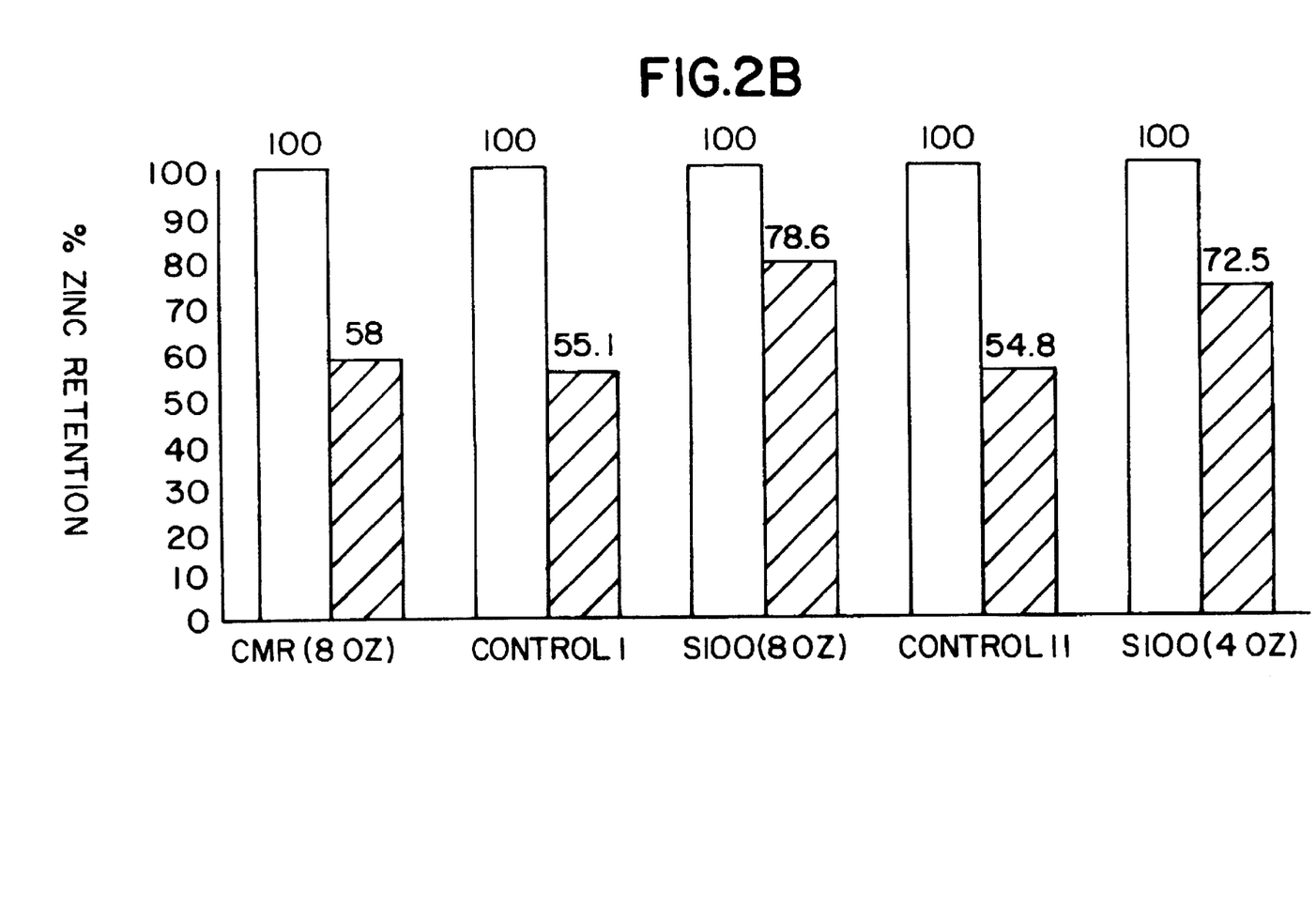
FIG. 2B amplifies the comparison of FIG. 2A by normalizing the one-month Zn level (solid) and expressing the three-month retention levels as a percentage thereof (////)
Figure 3:
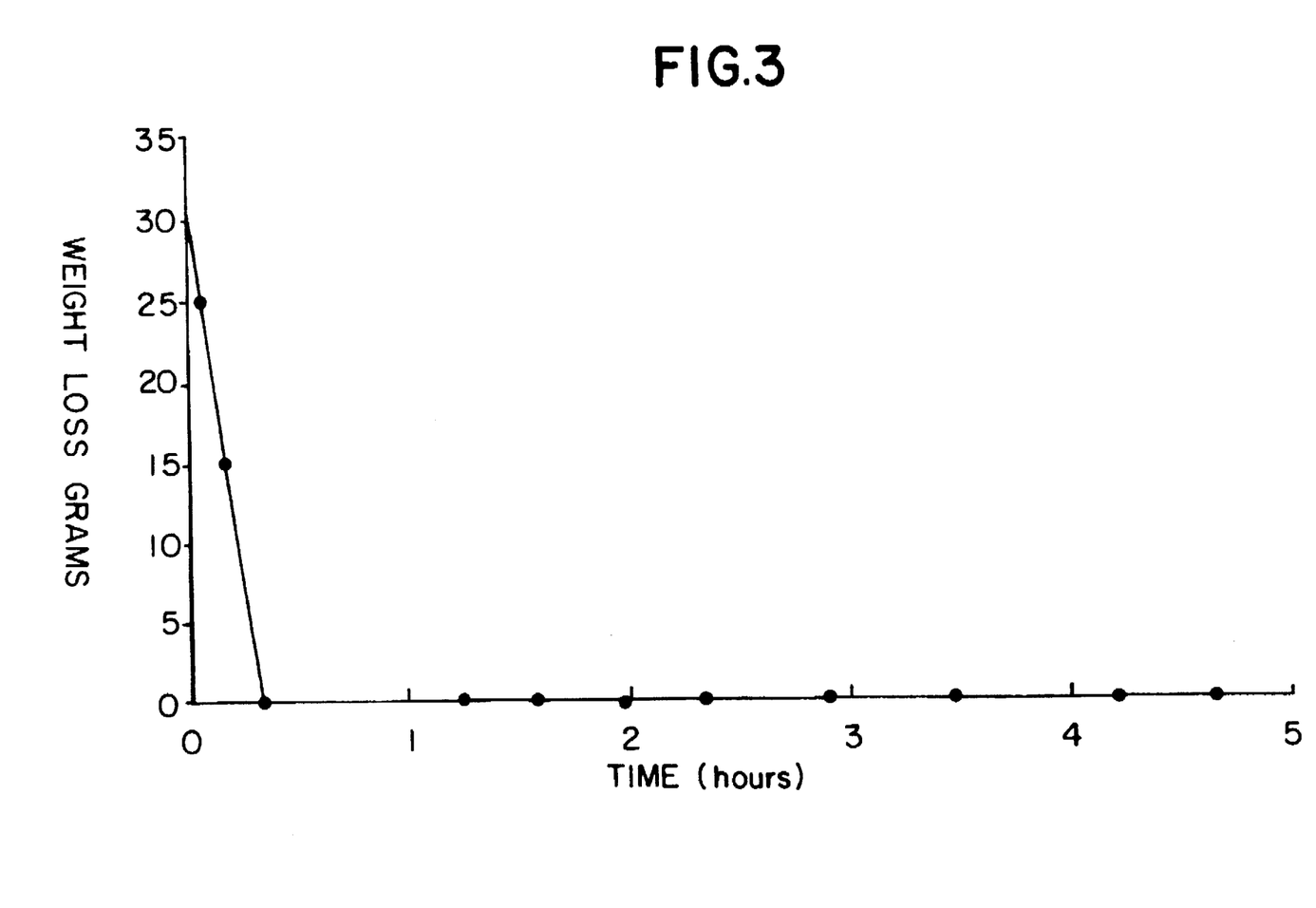
FIG. 3 plots the loss of methyl bromide over time upon exposure to the open atmosphere.
Figure 4:
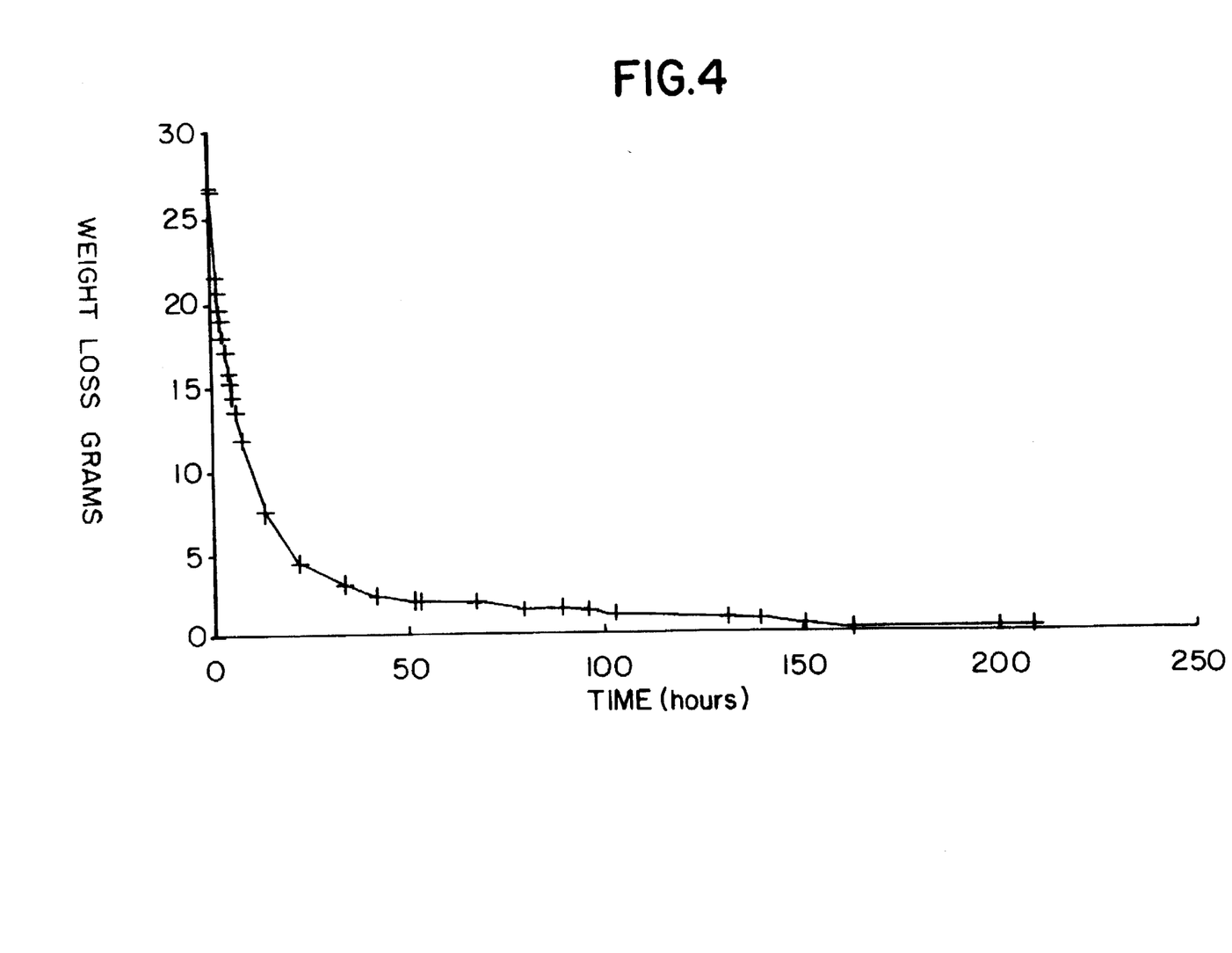
FIG. 4 tracks loss of methyl bromide from a corn oil/polyisobutylene solution, over time.
Figure 5:
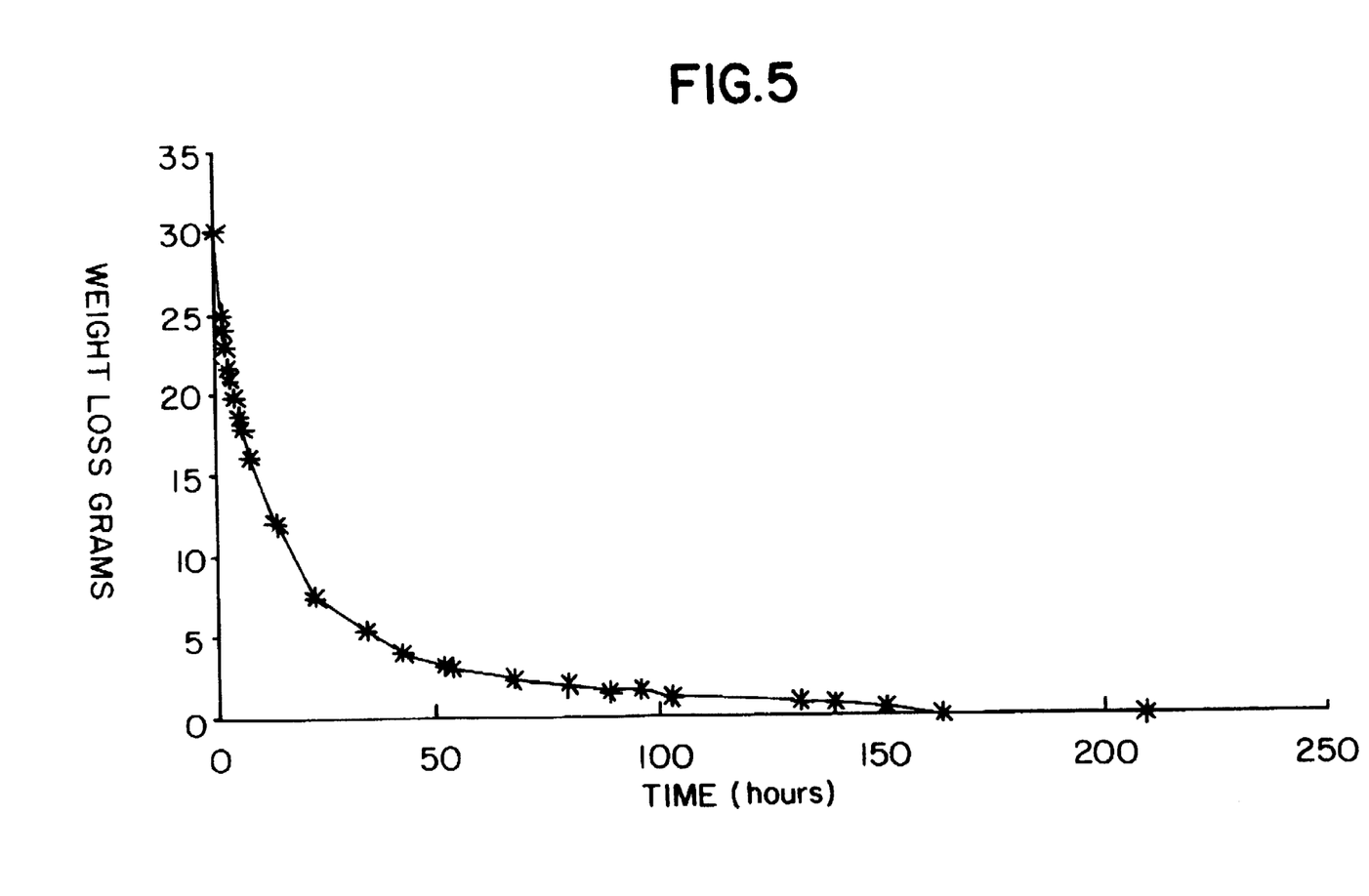
FIG. 5 records the loss of methyl bromide from neat polybutene, over time.

The raw data of FIG. 2A and normalized data of FIG. 2B show that the sticker/spreaders of this invention enhance effectiveness of treatment by increasing longevity of the active material/ingredient on the leaf. As compared to treatment with the CMR standard, the same concentration of the DPI S100 sticker/spreader of this invention affords, after three months, a 23% increase in Zn retention. Use of the DPI S100 composition at a concentration one-half that of the CMR standard provides a 14.5% increase in Zn retention after three months. Because total Zn content was measured without distinction as to that present on the leaf surface and that transported into the leaf, a reasonable inference is that any increase in detectable levels is a reflection of longer surface retention in any event.

The following examples illustrate use of the inventive polyolefin compositions to control the release of an active material. As described above, these compositions can be used as aqueous emulsions, but can also be employed neat or diluted with a suitable organic solvent—depending upon the molecular weight. By way of illustration, methyl bromide was chosen as the active material. Methyl bromide is a volatile gas at room temperature and used in the agricultural industry as a soil fumigant/pesticide. Under typical field procedures, the methyl bromide is injected into the soil as a gas, while the soil is simultaneously covered with an appropriately impermeable plastic tarp or plastic film to ensure sufficient contact time and pesticidal activity. Treating large fields in this manner is very costly and time consuming, requiring sophisticated equipment. The following examples show the present invention to afford distinct advantages over the prior art.

EXAMPLE 3

As a control, 30 grams of methyl bromide was placed in a sealed eight inch square glass container, placed on balance, then exposed to the atmosphere at room temperature. FIG. 3 shows the weight loss of methyl bromide observed as a function of time.

Approximately 30 grams of methyl bromide was dissolved in 200 grams of a 1:1(w/w) solution of a commerical corn oil and polyisobutylene (MW=1,000). The methyl bromide/polyolefin composition was placed in a sealed eight inch square glass container, place on a balance, and exposed to the atmosphere at room temperature. Inasmuch as neither the oil nor the polyolefin are volatile or reactive, FIG. 4 shows the weight loss of methyl bromide observed as a function of time. With comparison to FIG. 3, it is seen that the inventive polyolefin controls the release of methyl bromide, increasing potential contact time and enhancing its pesticidal activity.

EXAMPLE 4

Approximately 30 grams of methyl bromide was dissolved in 200 grams of neat polybutene (MW=1,000). This solution was placed in a sealed eight inch square glass container, placed on a balance, then exposed to the atmosphere at room temperature. Again, because the polyolefin is non-volatile and non-reactive, FIG. 5 shows the weight loss of methyl bromide observed as a function of time. As shown with the previous example, a significant amount of methyl bromide is available for a longer period of time, thereby promoting its effect as a fumigant/pesticide.

As observed with the previous example, only negligible amounts of methyl bromide remain after 4–5 days. Because prolonged contact with methyl bromide can be detrimental to plant growth and/or the harvestable crop, the depletion observed meets another crucial requirement of soil fumigation.

EXAMPLE 5

The utility of two sticker/spreader combinations of the present invention was demonstrated in conjunction with a winter weed treatment and, simultaneously, compared with the CMR product of the prior art. In this example cacodylic acid, a contact herbicide, is the active material. (A commercial preparation of cacodylic acid is available under the MONTAR tradename from Monterey Chemical Company of Fresno, Calif.) Contact herbicides are useful for demonstrating improved longevity and retention, isasmuch as these factors are critical to their effectiveness. As indicated on the manufacturer's label instructions, cacodylic acid—as with other contact herbicides—are most effective when applied under sunny conditions.

Four herbicidal mixtures were prepared, each including the commercial MONTAR product, an aqueous solution of cacodylic acid in sufficient amount to afford 7.44 pounds of the active ingredient per acre. MONTAR was used alone on a 6×100 foot lot populated by a mixture of grass and broadleaf weeds. Test plot No. 1 (6×100 feet) was sprayed with a CMR-modified (16 fluid ounces per 100 gallon tank mix) MONTAR product. Test plot No. 2 (6×100 feet) was sprayed with DPI S100-modified (16 ounces per 100 gallon tank mix) MONTAR product. Test plot No. 3 (6×100 feet) was sprayed with DPI S200-modified (16 fluid ounces per 100 gallon tank mix) MONTAR product. On all test plots, as with the control plot, a backpack type carbon dioxide sprayer with a hand-held wand and a six foot, 4-nozzle spray boom was utilized. It should be understood that the test of this example was initiated under cold, wet weather conditions—less than ideal for contact herbicides.

The efficacy of each MONTAR spray applied was evaluated by the rate of kill, on a scale of 0 to 10, with 0 indicating no weed kill whatsoever and 10 indicating total kill (i.e., bare ground). The control and test plots were observed daily for two weeks, then weekly for three months. The results, with numerical ratings, are summarized below in Table 1

Table 1.

1. Intial Kill (Weeds Dead or Severely Yellowed at 7 days):
   Control plot—2.
   CMR Spreader/Sticker—5.
   DPI S100 Sticker/Spreader—6. *
   DPS S200 Sticker/Spreader—6. *
   * The DPI-treated plots showed signs of weed kill earlier than did CMR and Control plots.
2. Final Kill After 2 weeks (Maximum Kill attained with Trail):
   Control—3.
   CMR Spreader/Sticker—6.
   DPI S100 Sticker/Spreader—8.
   DPI S200 Sticker/Spreader—8.
3. Longevity of Weed Kill After 3 months:
   Two and three months after spraying, plots were re-observed to determine the return of weed growth. The Control plot was indistinguishable from the surrounding, unsprayed field, without indication that the plot had been sprayed. The CMR treated plot weeds had largely grown back, although faint outlines of the spray area were detectable. The DPI S100 and S200 plots still had very noticeable weed knockdown, with the plots clearly delineated, as compared to the surrounding field, by their lack of weed regrowth.
   Control—0.
   CMR Spreader/Sticker—1.
   DPI S100 Sticker/Spreader—6.
   DPI S200 Sticker/Spreader—6.

While the principles of this invention have been described in connection with specific embodiments, it should be understood clearly that these descriptions are made only by way of example and are not intended to limit the scope of the invention, in any manner. For example, the techniques, sticker compositions, spreader compositions, sticker/spreader combinations, and active materials available can be employed by those skilled in the art in a fashion analogous to those described herein to treat a wide variety of plants and/or enhance plant growth. While several examples are provided by way of demonstrating the type of plant, active material, sticker, and/or sticker/spreader compositions contemplated by the present invention, other useful combinations are available through well-known formulation techniques and application processes. As such, the present invention can be extended with beneficial results to the retention and dispersion of various protective coatings on numerous fruit and vegetable varieties for protection from excessive heat, cold or sun exposure. For instance, a kaolin/clay composition available under the SNOW trademark from the Wilbur-Ellis Company of Fresno, Calif., can be used in conjunction with the present invention when formulated and applied as described herein. The resulting combination enhances solar reflectance and reduces crop damage, sunburn and sun scald. While the efficacy of the inventive polyolefins has been demonstrated with spiders and spider mites, the present invention also extends to the use thereof for the extermination of other insects predisposed to such non-toxic substances. Other advantages and features of the invention will become apparent from the claims hereinafter, with the scope of the claims determined by the reasonable equivalents, as understood by those skilled in the art.

Advantages of the Invention

As discussed above, a sticker of the present invention used alone or in combination with a spreader component enhances the effect achieved through use of an active material such as a herbicide, pesticide, fungicide, rodenticide, nutrient, plant growth regulator, pheromone, defoliant and the like. The inventive polymeric compositions, sticker/spreader combinations, and adjuvants of the present invention are effective in lower dosages than otherwise available through the prior art, are compatible with active materials with respect to handling and application techniques, dissolve or emulsify readily in an appropriate organic or aqueous solvent, and are stable over long storage periods. When used alone or in combination with a spreader component, the polyolefins of the present invention enhance the retention of an active material on a plant or other surface by increasing the resistance to removal by wind, water, and/or mechanical action. When used in combination with the inventive polyolefins and in accordance with this invention, various spreader components ensure adequate coverage of the polyolefin in a homogeneous manner over the entire surface area. In such a way, the sticker and spreader components of the present invention act synergistically to improve the performance and cost-efficiency of the active material. Savings are further realized through lower quantities and/or concentrations of the sticker and/or sticker/spreader combinations required to achieve good results.

We claim:

1. The method of treating soil and vegetative surfaces which comprises coating these surfaces with an active material selected from the group consisting of insecticides, herbicides, fungicides, rodenticides, nutrients, plant growth regulators, pheromones and defoliants which active material is combined with an adjuvant composition which is an emulsion comprising an aqueous phase which contains a surfactant and a polymer consisting essentially of a methyl-substituted polyolefin having a molecular weight of about 300–30,000, whereby the active material is distributed more evenly over the soil and vegetative surfaces and is retained thereon for a longer period of time.

2. The method of claim 1 wherein the methyl-substituted polymer has a molecular weight of about 900–3000.

3. The method of claim 1 where the methyl-substituted polyolefin is selected from the group consisting of isobutylene homo- and co-polymers.

4. The method of claim 3 where the methyl-substituted polyolefin is an isobutylene co-polymer containing monomers selected from the group consisting of butylene, styrene, butadiene, isoprene and combinations thereof.

5. The method of claim 4 where the monomer is a butylene.

6. The method of claim 1 where the active material is an insecticide.

7. The method of claim 1 where the active material is a pheromone.

8. The method of claim 1 where the active material is a nutrient.

9. The method of claim 1 where the active material is a fungicide.

10. The method of claim 1 where the active material is a rodenticide.

11. The method of claim 1 where the active material is a plant growth regulator.

12. The method of claim 1 where the active material is a defoliant.

* * * * *